United States Patent [19]

Saville

[11] Plant 5,145

[45] Nov. 29, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 411,358

[22] Filed: Aug. 25, 1982

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety with lemon yellow flowers edged with Dutch vermilion red.

1 Drawing Figure

The present invention relates to a new and distinct variety of rose plant of the miniature rose class, which was originated by my crossing as seed parent an unknown, unpatented, miniature climbing seedling of my creation and an unknown, unpatented miniature seedling of my creation as pollen parent. The denomination of this rose is "Savagen".

Among the novel characteristics possessed by this new variety which distinguish it from its parents and all other varieties of which I am aware are unusually attractive lemon yellow flowers edged with vermilion red that remain colorfully attractive as flowers age. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "40A" is plate 40A of The Royal Horticultural Society Colour Chart.

Parentage: Seedling.

*Seed parent.*—My unpatented, unreleased climbing miniature seedling.

*Pollen parent.*—My unpatented, unreleased miniature seedling.

Class: Miniature.

The following observations are made of specimens grown outdoors in Essex County, Mass. during the month of June.

1. FLOWER

Blooming habit: Profuse, continuous.

A. Bud:

(1) *Size.*—Medium.

(2) *Form.*—Short, ovoid.

(3) *Color.*—After sepals fall, petal edge 40A, lower $\frac{3}{4}$ of petal 13A.

(4) *Sepals.*—Smooth, much longer than bud with minor foliation.

(5) *Peduncle.*—Length — About $\frac{5}{8}$ inch. Aspect — Straight. Strength — Erect. Color — Near 146D.

B. Bloom:

(1) *Size.*—Average size when fully expanded — about $1\frac{1}{2}$ to $1\frac{3}{4}$ inches.

(2) *Borne.*—Singly and large clusters.

(3) *Form.*—Cupped, globular becoming flat, outer petals quill to points.

(4) *Petalage.*—Number of petals under normal conditions — about 35 to 40.

(5) *Color.*—As sepals fall, red and yellow colored blooms open retaining similar coloring until flowers age. Petal coloring is lemon yellow 13A edged with Dutch vermilion red 40A. Edge coloring envelopes petals as unfurling petals are exposed to sunlight and age. Color of petals at point of attachment is near 13A. In aged blooms, red coloring mutes to near 43C and yellow coloring tends to whiten to near 13D. General tonality of $\frac{1}{3}$ to $\frac{1}{2}$ open blooms appears essentially deep yellow with vermilion red edged outer petals.

C. Petals:

(1) *Texture.*—Medium.

(2) *Appearance.*—Inside and outside — satiny.

(3) *Form.*—General fan shape but quill as reflex to points.

(4) *Arrangement.*—Regularly arranged, shingle-like.

(5) *Petaloids in center.*—Few.

(6) *Persistence.*—Drop off cleanly.

(7) *Fragrance.*—Slight, spicey.

(8) *Lasting quality.*—Medium lasting on plant and as cut flower.

2. REPRODUCTIVE ORGANS

A. Stamens, filaments and anthers:

(1) *Arrangement.*—Stamens regularly arranged around styles.

(2) *Color.*—Near 14A.

B. Pollen:

*Color.*—Near 15A.

C. Styles: Even, medium length.

D. Stigmas:

*Color.*—Near 60B.

E. Hips: None observed.

3. PLANT

A. Form: Upright, compact, bushy.

B. Growth: Vigorous.

*Height attained.*—About 14 to 16 inches.

C. Foliage: Compound 5 to 7 leaflets.

(1) *Size.*—Medium.

(2) *Quantity.*—Abundant.

(3) *Color.*—New foliage: Upper side — Near to 137B but some wine colored 187B. Under side — Near to 138B lightly edged with 187B. Old foliage: Upper side — Near 137A. Under side — Near 147B to 148C.

(4) *Shape.*—Oval.

(5) *Texture.*—Upper side is slightly glossy and under side is matte.

(6) *Edge.*—Serrated.

(7) *Serration.*—Regular.

(8) *Leaf stem.*—Color — Near to 147B. Under side — near to 144A.

(9) *Stipules.*—Medium.

(10) *Resistance to disease.*—Blackspot — Average. Mildew — Average. Rust — Average.

D. Wood:

(1) *New wood.*—Color — Near 187B. Bark — Smooth.

(2) *Old wood.*—Color — Near 138B. Bark — Smooth.

E. Thorns:

(1) *Thorns.*—Quantity (main stalk) — Very few. On laterals from stalk — None. Form — Pointed, curved slightly downward. Length — Medium. Color — Reddish green. Position — Scattered.

(2) *Prickles.*—None.

F. Winter hardiness: Needs winter protection in severe climate.

I claim:

1. A new and distinct variety of rose plant of the miniature rose class, substantially as shown and described, characterized particularly by bright lemon yellow flowers edged with Dutch vermilion red borne singly and in large clusters on a vigorous, upright growing plant.

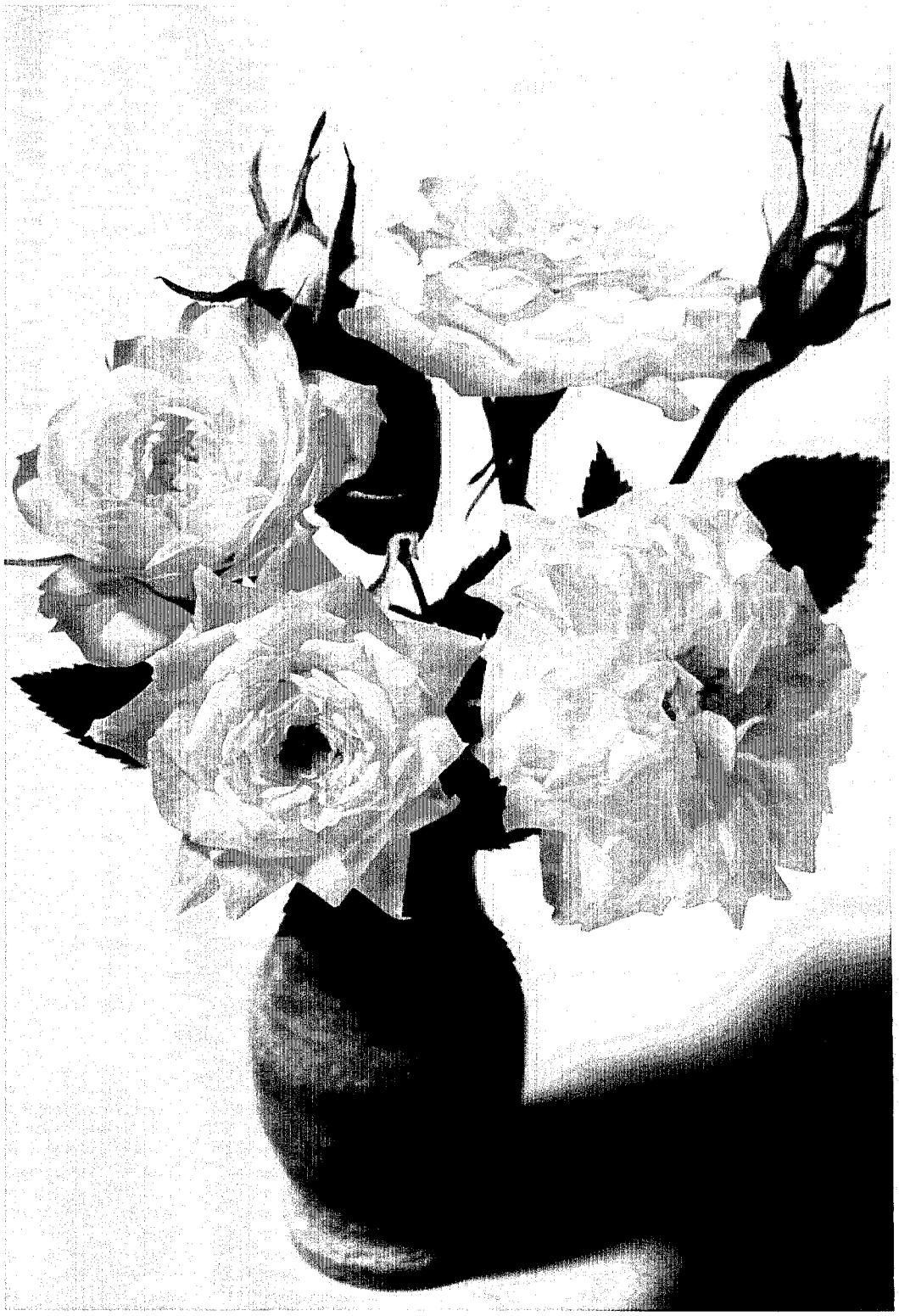

* * * * *